United States Patent [19]

McCormick

[11] Patent Number: 5,616,227

[45] Date of Patent: Apr. 1, 1997

[54] METHOD FOR EXTENDING THE LIFE OF ELECTROPHORETIC GELS

[75] Inventor: Randy M. McCormick, Santa Clara, Calif.

[73] Assignee: Dionex Corporation, Sunnyvale, Calif.

[21] Appl. No.: 494,940

[22] Filed: Jun. 26, 1995

[51] Int. Cl.$^6$ .............................. C25B 15/00; G01N 27/26
[52] U.S. Cl. ........................... 204/457; 204/456; 204/607; 204/608
[58] Field of Search ..................... 204/182.8, 299 R, 204/457, 466, 450, 606, 607, 608, 616, 456

[56] References Cited

U.S. PATENT DOCUMENTS

| | | | |
|---|---|---|---|
| 4,224,529 | 9/1980 | Fujiwara | 307/127 |
| 4,865,706 | 9/1989 | Karger et al. | 204/182.8 |
| 4,865,707 | 9/1989 | Karger et al. | 204/182.8 |
| 4,997,537 | 3/1991 | Karger et al. | 204/182.8 |
| 5,041,203 | 8/1991 | Serwer | 204/299 R |

OTHER PUBLICATIONS

U. Grossbach *Biochim. Biophys. Acta*, 107 (1965) 180–182.
J. Jorgenson, K.D. Lukacs, *Anal. Chem.* (1981) 53, 1298–1302.
J. Prober, et al. *Science*, 238 (1987) 336–341.
L.M. Smith et al. *Nature*, 321 (1986) 674–679.
H–F Yin et al. *J. High Res. Chromatogr.* 13 (1990) 624–627.
Raymond, S., "Science", 18 Sep. 1959, p. 711.
Guttman, A., Anal. Chem., 1993, 65, 199–203.
Carle, G., Science, v. 232, pp. 65–68.
Hjertén, S., J. Chrom., 270 (1983) 1–6.

*Primary Examiner*—Kathryn Gorgos
*Assistant Examiner*—Alex Noguerola
*Attorney, Agent, or Firm*—Flehr, Hohbach, Test, Albritton & Herbert

[57] ABSTRACT

A method for extending the useful lifetime and improving the reproducibility of electrophoresis gels, particularly gel-filled capillaries. The polarity of the applied electric field imposed across the gel is periodically reversed between one or more electrophoretic runs.

10 Claims, 11 Drawing Sheets

Normal Gel Orientation

Figure 6b

Reversed Gel Orientation

Figure 6C

Back to Normal Gel Oreintation

METHOD FOR EXTENDING THE LIFE OF ELECTROPHORETIC GELS

BACKGROUND OF THE INVENTION

Separation of macromolecules by gel electrophoresis is a well established technique. The technique has demonstrated utility for the separation of various types of biomacromolecules such as deoxyribonucleic acid (DNA), ribonucleic acid (RNA), oligonucleotides, proteins, peptides, etc. and permits separation of mixtures of these materials into isolated, discrete bands for analytical or preparative purposes. A basic requirement of the electrophoretic gel is that it must have a porous network through which the charged analyte biomolecules can migrate; because of differences in size of the macromolecule of varying molecular weight, species of differing sizes migrate through the gel with differing velocities. Large molecules experience more difficulty traversing the porous network presented by the gel and thus move with lower velocities relative to smaller molecules which can more easily penetrate the pores of the matrix and thus move with greater velocities relative to larger molecules. Numerous types of materials are useful for preparing the gel matrix. One requirement of materials used to form gels is that it must form a stable porous matrix, incorporating a large amount of water in the pores of the matrix.

Gel electrophoresis can be performed in numerous formats. These include open horizontal (submarine) slab and closed vertical slab gel formats as well as a cylindrical tube gel format. In any of these formats, the steps for performing an electrophoretic analysis consist of preparation of the gel in a casting container characteristic of the particular format, followed by application of the sample to be analyzed to the gel. Subsequent application of a constant electrical field (either constant voltage, current or power) across the gel causes differential migration of the components of the sample through the porous network formed by the gel to separate into discrete bands of essentially pure components. The separated component bands are then visualized by removing the gel (either tube gel or slab gel) from its original casting container and immersion of the gel into some visualization reagent such as Coomassie Blue stain, silver stain, ethidium bromide, etc.; these visualization agents are chosen to have a differential affinity for the sample components of interest relative to the polymeric material used to form the gel and thus the separated bands preferentially interact with the staining agent.

In some cases, it is necessary to destain the gel by immersing it in another reagent solution which extracts the background staining agent from the bulk of the gel while retaining the staining agent adsorbed or deposited onto the separated sample component bands. As a final step, a permanent record is made of the separation pattern by either removing the water from the gel to yield a dry, transparent record of the gel which can be photographed, autoradiographed, or used as is for a permanent record.

In all of these previous cases, the gel is cast, used for analysis, removed from casting vessel, chemically treated for visualization of the separation, and then dried. Because of the manipulations and treatments with various reagent solutions, it is not possible to reuse the gel for multiple consecutive analyses. Stability and reuse of classical electrophoretic gels is thus rarely an issue and gels used in these formats are treated as single-use, disposable items.

In the classical formats of gel electrophoresis, the electrophoretic separation is performed under a controlled and constant electrical field. Typically, an electrical field is applied across the gel and controlled by maintaining either the applied potential, the current or the power (arithmetic product of voltage and current) constant for the duration of the separation. In recent years, periodic inversion of the electrical field across agarose slab gels has been implemented [G. F. Carle, M. Frank, M. V. Olson, *Science*, (1986) 232 65–68] as a way of permitting enhanced resolution in the separation of very large (chromosomal size) DNA molecules on such gels. This field inversion was performed to facilitate reorientation of these large molecules in the gel during periods of field inversion and thus prevent separation of the molecules through the gel which would prevent separation of such large molecules. Carle et al. discloses a simple-use gel format.

In recent years, an extension of the tube gel format of electrophoresis has evolved into the use of small diameter (capillary) tube gels. Originally described by U. Grossbach [*Biochim. Biophys. Acta*, 107 (1965) 180–182] and improved upon in recent years by S. Hjerten [*J. Chromatogr.* (1983) 270 1–6] and B. Karger et al. [U.S. Pat. Nos. 4,865,706, 4,865,707, 4,997,537], these gels offer numerous advantages over the older, thick-gel formats mentioned above. A significant improvement in the development of capillary gels, which evolved from free zone electrophoretic separations [J. Jorgenson, K. D. Lukacs, *Anal. Chem.* (1981) 53 1298–1302], is the use of on-line detection technologies for visualization of the separated analyte bands. Thus, with the development of capillary gel electrophoresis, reusability of the gel for multiple separations became desirable for several reasons. Firstly, the gel is never removed from its casting vessel or treated with visualization agents to detect the separated bands. A section of the capillary gel is used as an absorbance or fluorescence cell in the optical path of the appropriate detector which detects all components which migrate by the detector. In practice, reuse of the gel for multiple, consecutive analyses is possible. This permits the gel elution pattern to be calibrated against an appropriate standard mixture. Thus, the gel could be reused for multiple determinations of molecular weights of proteins or the base (or base pair) size of oligonucleotides, RNA and single or double-stranded DNA.

An object of this invention is to provide an improved protocol for extending the utility of electrophoretic gels in general, and capillary electrophoretic gels in particular, thus permitting a greater number of analyses to be achieved on a single gel.

Another object is to improve the analytical precision of capillary electrophoretic gels by reducing the run-to-run variation in migration times for analyte bands to reach the detector.

SUMMARY OF THE INVENTION

In accordance with the present invention, a method for gel electrophoresis, preferably of the capillary type, is disclosed in which the useful life of the gel is extended by periodic reversal of the polarity of the applied electric field along the gel. In one embodiment, the sample is deposited at one end of an electrophoretic gel flow path, and voltage is applied along the flow path to separate the macromolecules which are detected and eluted. Then, the polarity of the electric field is reversed. Thereafter, the macromolecules of a second sample are separated by depositing the sample at either end of the gel flow path while applying an electric field. The separated macromolecules are then detected. Multiple samples may be electrophoretically separated prior to reversal of the field.

In another embodiment, a first sample is electro-phoretically separated along an electrophoretic gel flow path. The macromolecules are detected and eluted. Then, a second sample is separated by depositing it at the opposite end of the flow path from the first sample. An electric field is applied along the gel flow path of opposite polarity to that of the first sample and the macromolecules are detected.

DETAILED DESCRIPTION OF THE PREFERRED EMBODIMENTS

The present invention extends the lifetime of reusable electrophoretic gels by periodic reversals of the polarity of the electric field between or after electrophoretic separations of different samples. In a preferred embodiment, the gel is disposed in a conduit, more particularly in the bore of a capillary. Accordingly, unless otherwise specified, the specific description will be with respect to capillary gel electrophoresis even though the invention is broadly applicable to either gel forms (e.g. slabs).

Figure 1:
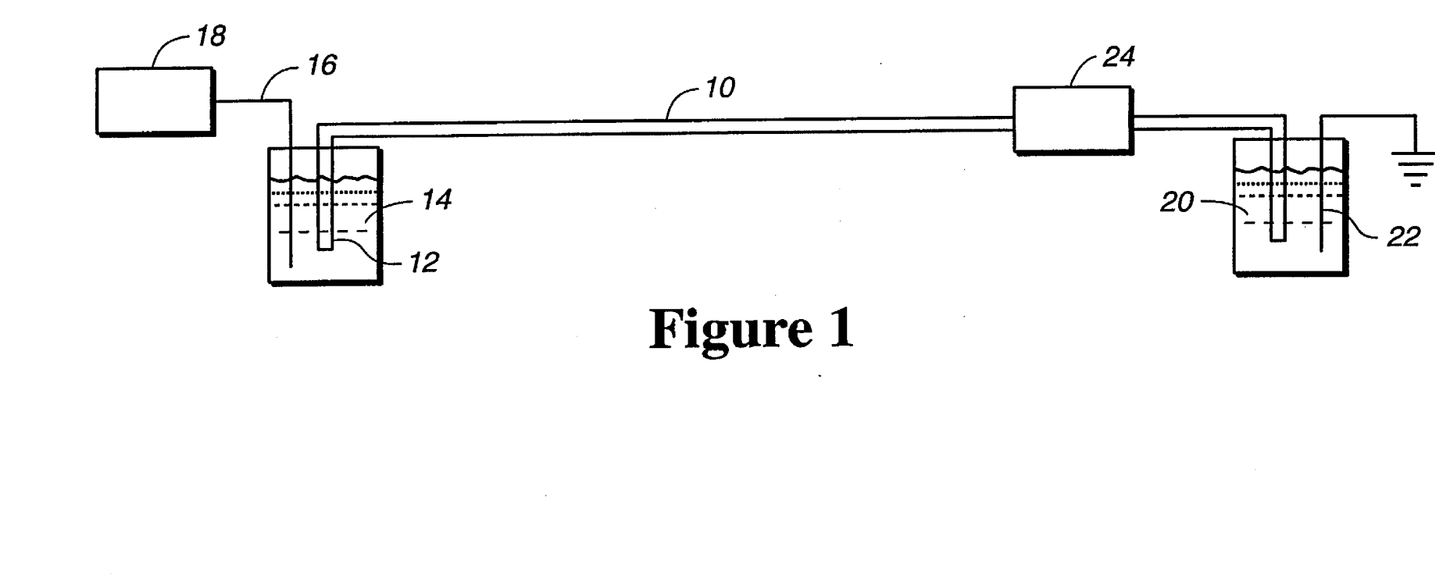
FIG. 1 is a schematic diagram of a conventional capillary electrophoresis system suitable for performing the method of the present invention.
Figure 2A:
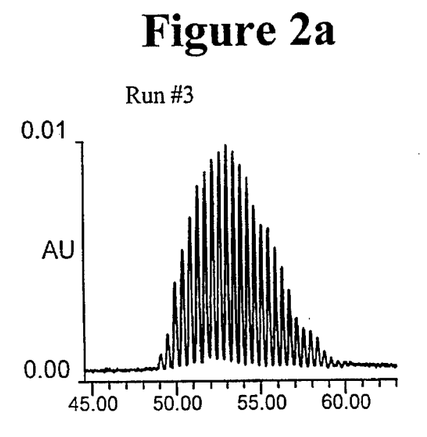
FIGS. 2A–D is an electropherogram of separated macromolecules illustrating prior art gel deterioration.
Figure 2B:
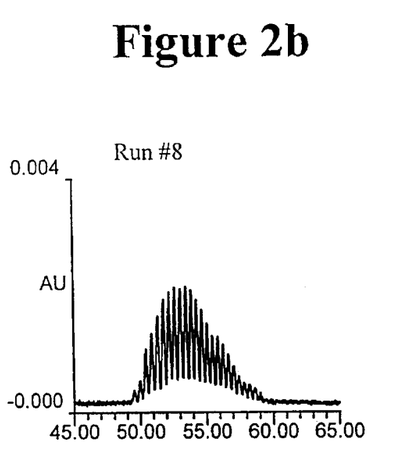
Figure 2C:
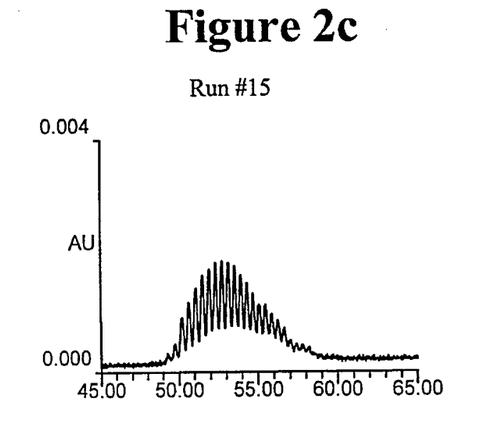
Figure 2D:
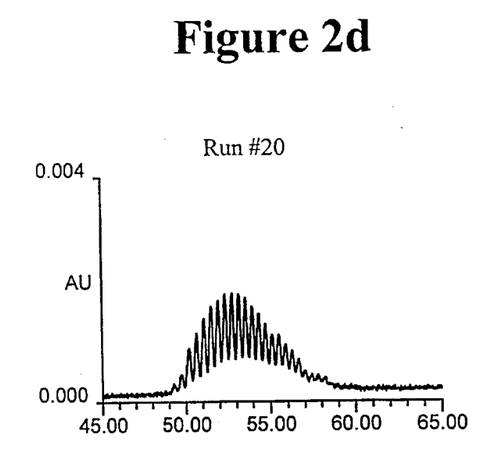

A typical CE system is illustrated in FIG. 1. The capillary electrophoretic separating system typically includes a small bore capillary 10 filled with a gel. A first end 12 of capillary 10 is immersed in an electrolyte reservoir 14. Also contained within this reservoir is a first electrode 16 connected to a high voltage supply unit 18. The second end of capillary 10 is in communication with a second reservoir 20 which is in contact with a second electrode 22 to complete the high voltage circuit. A detector 24 (e.g. a fluorescence detector) is disposed to detect the macromolecules on the gel through the capillary (or downstream in an embodiment not shown).

One of the most commonly used materials for forming gels, described by Raymond and Weintraub (Science, 130 (1959) 711) is cross-linked polyacrylamide. A polyacrylamide gel may be formed by copolymerizing acylamide monomer with a cross-linking agent such as N,N'-methylenebisacrylamide (bis-acrylamide) in an aqueous solution containing one or more electrically-conductive salts as background electrolyte. The acrylamide and bis-acrylamide monomers are caused to react by addition of a free-radical initiator agent such as ammonium persulfate and a catalyst agent such as N,N,N',N'-tetramethylethylenediamine (TEMED); upon polymerization, the acrylamide/bisacrylamide polymer forms a stable gel structure containing up to 95% or more of water in the pores of the gel.

Other agents used for forming gels are hydrophilic polymeric materials such as agarose or starch; both are high molecular weight polymers, which, upon dissolution by heating in water at low concentrations (1% or less) and subsequent cooling, will form stable porous gels. The size of the molecules to be separated determines which of these materials is used to form the gel, with acrylamide the preferred material for separation of low molecular weight species and agarose for high molecular weight molecules.

The present method is applicable to the separation of macromolecules capable of being separated and detected by gel electrophoresis. Such macromolecules include biologically derived macromolecules ("biomacromolecules") (e.g. DNA, RNA, oligonucleotides, peptides, proteins, oligosaccharides, complex carbohydrates, glycoproteins, and monosaccharides.

The present invention is based on the hypothesis that the reason for a decrease in performance with time and an improved performance with polarity reversal is a change in the gel structure. The gel starts as a random network of gel polymers with an approximately even distribution of pore sizes. As the gel is exposed to the electric field and since it is partially ionized (e.g. polyacrylate gel), the polymer strands begin to orient with the field. This is believed to cause the distribution of pore sizes to change and negatively affect resolution. One possibility is that the average pore size increases with polymer orientation with the electric field causing lower molecular weight analyte resolution to degrade first. Alternatively the average pore size decreases causing a decrease in resolution of the higher molecular weight analyte molecules. It is recognized that orientation of the polymer with the electrical field occurs and affects resolution as discussed in A. Guttman et al. (Anal. Chem., 65 (1993) 199–203).

In a first embodiment, one or more samples may be run with the electric field being of the same polarity before reversing the field. The choice is dependent on the parameters of the system. The optimum performance of the gel is maintained using the same magnitude and duration of reverse potential as is used during separation. Thus, the reversal could be after each injection for a time equal to the full run time. Alternatively, many samples may be run without polarity reversal (e.g. for eight hours) and then the polarity may be reversed for the same length of time overnight when no samples are being run. The choice may be made on the basis of convenience of instrument configuration. For example, if the normal run is ten minutes in duration, the polarity is suitably reversed after each run. On the other hand, if a typical run is 60 minutes, one might choose to run without polarity reversal during the day and to perform the total reversal overnight.

In the above embodiment, the method for gel electrophoresis typically includes the following steps:

(1) electrophoretically separating the macromolecules in a first sample along an electrophoretic gel flow path by depositing the first sample at a first end of the flow path and applying an electric field along the flow path, (2) detecting the separated macromolecules in the first sample, (3) eluting the separated macromolecules from the gel flow path, (4) applying an electric field along the gel flow path of opposite polarity, (5) electrophoretically separating macromolecules in a second sample by depositing it at one end of the flow path while applying electric field along the flow path, and (6) detecting the macromolecules in the second sample.

The condition of electrophoretic separation of the first sample may be the same as those used in conventional gel electrophoresis.

In a second embodiment, application of the opposite electric field may be accomplished simultaneously with separation of the macromolecules in a second sample. In this instance, the macromolecules of the first sample are electrophoretically separated as in the first embodiment by depositing at a first end of the capillary and applying electric field along the gel path. The macromolecules are separated and detected. Then the macromolecules of a second sample are electrophoretically separated by applying the sample at the second end of the capillary and applying an electric field along the gel flow path of opposite polarity. While this has the advantage of continuous use of the instrument, it would require changes in the operation of a typical CE instrument. Specifically, to allow injection from either end of the capillary would require modification of the auto-sampler of a conventional analytical instrument which only permits interface with one end of the capillary. However, a person of ordinary skill could build an instrument to accommodate injections from either end thereby nearly doubling sample throughput while using the polarity reversal principle.

While the maximum benefit of the second embodiment is obtained by reversal for the same time and at the same current magnitude as during separation, some benefits are obtained if such reversal is not for the same duration. Thus, for similar electric fields, it is preferable that the reversed electric field be applied at least 80% of the duration that the electric field is applied for the first separation, more preferably, 100% or more of the duration. Similarly, the magnitude of the field may be modified to shorten the time of the polarity reversal. The relationship between these two parameters is as follows. The field strength times the duration of application is approximately constant. Thus, one can double the field strength for half the application duration if shortening the regeneration time is desirable.

As indicated, the operator may use the gel continuously for electrophoretic separations during the course of the normal workday (8–10 hr.) and then, when the gel is not used for separations, the polarity across the gel would be reversed overnight such that voltage equal to but opposite in polarity would be imposed across the gel for a period of time approximately equal to the time period in which it was used during the day.

Another way to express the relationship between the time of application and intensity of the reversed electric fields is as follows. The product of the magnitude of the opposite potential and the duration of application should be at least 80% of the product of the magnitude of the previous electrophoretic separation times its time of application, preferably at least 90%, and most preferably 100% or more.

After polarity reversal in the above embodiment, the life of the gel and its corresponding resolution characteristics have been regenerated to substantially the same level as that of the original gel. Accordingly, a second sample may be separated on the gel by depositing it at either end of the gel while applying an electric field in either direction along the gel flow path. In all instances, the sample is eluted from the gel prior to running a second sample as in conventional capillary electrophoresis.

The separated macromolecules may be detected in accordance with conventional techniques. In a preferred method for capillary gel electrophoresis, the macromolecules are detected while the macromolecules are still contained within the gel (on-line). Such techniques include the use of a fluorescence or a UV/VIS type detector as illustrated in Anal. Chem. 65, 199–203 (1993). Alternatively, the macromolecules may be detected after elution from the gel, suitably by mass spectrometry as illustrated in F. Garcia and J. D. Henion, Anal. Chem. 64, 985 (1992).

One convenient way for reversing polarity is by an automated reversal of the electrical field with the capillary in the same disposition. Alternatively, the direction (orientation) of the capillary may be reversed without modifying the exterior application of the electric field.

Numerous mechanical and electrical devices are useful for accomplishing the reversal of field polarity across the gel. In the simplest implementation, polarity reversal can be implemented manually by the operator; at the end of each electrophoretic run or after a selected number of electrophoretic runs, the operator physically reverses the polarity applied across the gel by disconnecting the electrical leads connecting the electrophoretic gel to the electrical power supply and, if using a bipolar power supply, interchanging the leads to connections of opposite polarity to which they were connected during the electrophoretic run. If the operator is not utilizing a bipolar power supply, then the electrical leads to the electrophoretic gel may be connected to a power supply of opposite polarity to that used in the electrophoretic separation run.

Another method of accomplishing polarity reversal is to connect the electrophoretic gel to two power supplies of opposite polarity through a single-pole double-throw electrical relay. In this implementation, reversal of polarity can be accomplished manually by activating an electrical control signal which switches the relay between two pole positions which alternately connect the two power supplies to the electrophoretic gel.

In a further embodiment, reversal of the polarity can be achieved by use of a reversible polarity power supply which permits automatic selection of the polarity of the output from the supply.

Such power supplies are available from commercial suppliers; one example is Glassman High Voltage, Inc., Whitehouse Station, N.J. The two methods of reversing the polarity across the gel may be through the use of two power supplies of opposite polarity connected to the electrophoretic gel via a single-pole double-throw relay or alternatively through the use of a two-polarity power supply connected directly to the electrophoretic gel.

Several protocols exist whereby the reversed polarity procedure can be implemented to improve the performance of electrophoretic gels. In one implementation, the capillary gel is used for a number of consecutive, sequential electrophoretic separations and then the polarity across the gel is reversed for a determined period of time, preferably for a period of time and at an electrical field strength (volts/cm) equal to the period of time and field strength in which the gel was previously used for electrophoretic separations. Also, the gel may be used for one electrophoretic separation, following which the polarity across the gel is reversed such that an electrical potential equal to but opposite in sign is applied across the gel for a time duration approximately equal to that of the immediately previous separation run. As in the first embodiment, the time duration and the magnitude of the applied opposite potential preferably approximately equals the time duration of the previous run. The same mathematical relationship for variations between the times and intensifies of the reversed electric field described for the first embodiment also applies for the second.

Further, the polarity across the gel can be reversed not by altering the polarity of the electrical signals coming from the power supply but by changing the orientation of the gel such that under polarity reversal the original cathode end of the gel is immersed in the original anode buffer reservoir which is still connected to the anode electrode and the original anode end of the gel is immersed in the original cathode buffer reservoir which is still connected to the cathode electrode. An electrical field is now established across the gel by imposition of applied potential; however, now the direction of the polarity of the electrical field is effectively reversed since the orientation of the gel relative to the original electrical field is now reversed.

The polarity of the electrical field imposed across the gel may also be reversed in alternate runs while using the capillary for separation in each run. This is accomplished by placing two detector modules, one at each end of the capillary gel. An injection of sample is then made at one end of the capillary and the separation is allowed to develop and is monitored at the detection module at the end of the capillary opposite to the end where the injection is made. Upon completion of this separation, the polarity across the gel is reversed by interchanging (either manually or using a relay) the electrical leads from the power supply or changing to a power supply of opposite polarity. An injection is now made at the second end of the capillary and the separation is allowed to develop and is monitored using the detection module positioned at the end of the capillary opposite to that in which the injection is made. Upon completion of this separation, the third injection is made into the same end of the capillary as the first run; this alternation of injections is continued, each time using alternate ends of the capillary for injection and alternate detectors positioned at the end opposite to where the injection was made for detection. An improvement would be to use a translation device to transport the detection ends of the capillary into the optical path of a single detection module during alternate analyses, thus eliminating the need for two detection modules.

Polarity reversal is useful for extending the lifetime and improving the run-to-run reproducibility of various formulations of acrylamide gels. For purposes of illustration, 5% T 5% C gels were used throughout the examples illustrating the utility of the technique. However, the technique would also be useful for acrylamide gels of low concentrations (e.g. 1% T) and gels of high concentrations of monomers (e.g., 40% T). In addition, buffers other than the Tris-borate-EDTA (TBE) buffer system used here could be used with the polarity reversal protocols. Examples of other useful buffers would include but are not limited to Tris-acetate-EDTA, Tris-sulfate-EDTA, Tris-glycine, Tris-chloride, etc. Finally, the utility of polarity reversal could also be realized on gels formed from polymers other than acrylamide. Examples of other such polymers would include, but are not strictly limited to agarose, starch, celluloses, polyvinylpyrollidinone, etc. Those familiar with the art and science of electrophoresis could conceive of other examples beyond those cited here where polarity reversal would have demonstrated utility.

Implementation of the polarity reversal is readily accomplished in the gel-filled capillary format as described previously. In this format, detection of the separated analyte bands from the sample is accomplished on-line and separated bands are eluted from the capillary gel and into a large volume (relative to the volume of the capillary gel) of reservoir buffer, where the analyte band components become diluted and do not interfere with subsequent electrophoretic runs.

The polarity reversal protocol would also be useful for slab gel formats in which detection of separated analyte bands is done on-line. One example of such is a vertical slab-gel format which is commonly used with fluorescent detection for the separation of DNA sequencing fragments [J. Prober et al. *Science*, 238 (1987) 336 or L. M. Smith et al., *Nature* (London) 321 (1986) 674]; in both instances, detection is achieved on-line and analyte bands are eluted from the electrophoretic gel, leaving it ready for use in a subsequent analysis. The polarity reversal protocol might also be useful in the horizontal (submarine) slab-gel format, provided that subsequent to visualization of the separated bands, those bands are electroeluted from the gel, thus readying the gel for the subsequent analysis.

The following sets forth specific examples of the invention.

EXAMPLE 1

The following systems were used for the Examples.

High voltage power supplies of positive and negative polarities were from Glassman High Voltage, Whitehouse Station, N.J. The high voltage single-pole double-throw relay was from Kilovac Corporation, Santa Barbara, Calif. Gel-filled capillaries prepared in-house using silica capillary tubing (50, 75, or 100 μm id) from Polymicro Technologies, Phoenix, Ariz. Capillary gels were prepared by conventional protocols published in the scientific literature (e.g., H-F. Yin, J. A. Lus, and G. Schomburg, *J. High Res. Chromatogr.* (1990) 13 624–627). Acrylamide, bis-acrylamide, tris(hydroxymethyl)methylamine, boric acid, and EDTA used for gel preparation were from Hoeffer Scientific, San Francisco, Calif. Ammonium persulfate and TEMED were from Sigma Chemical Co., St. Louis, Mo. Alternatively, capillary gels were purchased from J&W Scientific, Folsom, Calif. Oligomeric polyadenosine samples ($PdA_{40-60}$) were from Pharmacia, Inc., Piscataway, N.J. 1X TBE buffer consists of 90 mM tris(hydroxymethyl)methylamine, 90 mM boric acid, and 2 mM ethylenediaminetetraacetic acid, disodium salt (disodium EDTA) in aqueous solution at pH 8.3+/−0.1. Experiments were performed on a commercial capillary electrophoresis instrument [Dionex Capillary Electrophoresis System I (CES I)].

EXAMPLE 2

This example illustrated of loss of resolution on capillary gel operated without polarity reversal.

FIGS. 2A–D illustrates the deterioration of resolution on a gel-filled capillary used for capillary electrophoresis operated under normal polarity conditions and without the benefit of polarity reversal. The capillary used in this experiment was a 65 cm length of 75 μm id fused silica capillary filled with a 5% T 5% C acrylamide gel containing 1X TBE and 7M urea as buffer. A sequential series of separations of $pdA_{40-60}$ oligonucleotides in water (0.01 units/mL) was made at 1 kV applied potential for 10 seconds followed by a running potential of 14 kV and 11 μA current. Detection of the elution profile of separated oligonucleotides was at λ-260 nm. The first few separations performed on this capillary exhibited satisfactory resolution as demonstrated by the profile shown in run #3 of FIG. 2A. However, by run #8, FIG. 2B, a loss in the resolution of the oligomer bands is evident. Loss of resolution continues with each successive separation (e.g., run #15, FIG. 2C) and by run #20, FIG. 3D, the resolving power of the capillary has essentially failed. The series of demonstration separations shown here is typical of those obtained on a gel-filled capillary operated for a successive series of run under normal polarity conditions and without the benefit of polarity reversal. Typically, capillary gels operated in this manner without the benefit of polarity reversal have a useful lifetime of <30 hours.

EXAMPLE 3

This example illustrates a gel-filled capillary operated under protocol of 12 hour normal polarity, 12 hour reversed polarity.

Figure 3A:
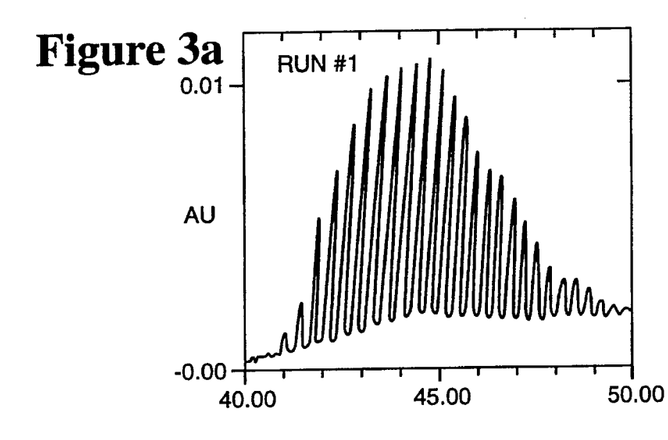
FIGS. 3A–F, FIGS. 4A–D, FIGS. 5A–5D, FIGS. 6A–6C, and FIGS. 7A–7B are electropherograms of separated macromolecules using polarity reversal according to the present invention.
Figure 3B:
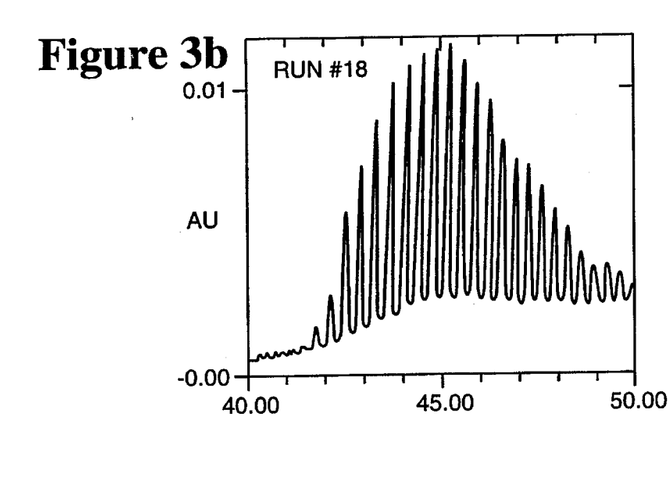
Figure 3C:
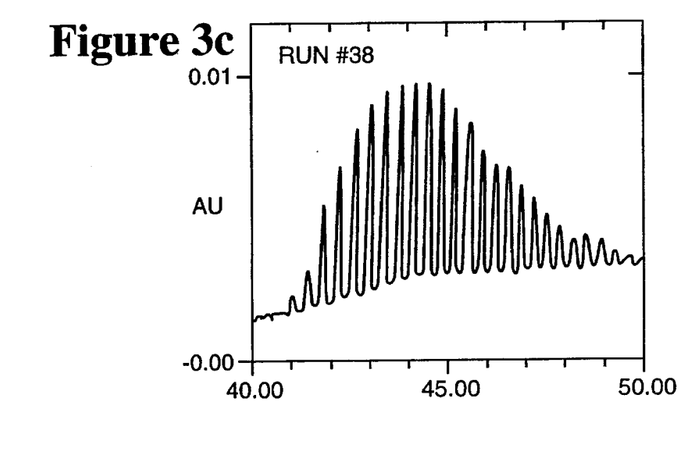
Figure 3D:
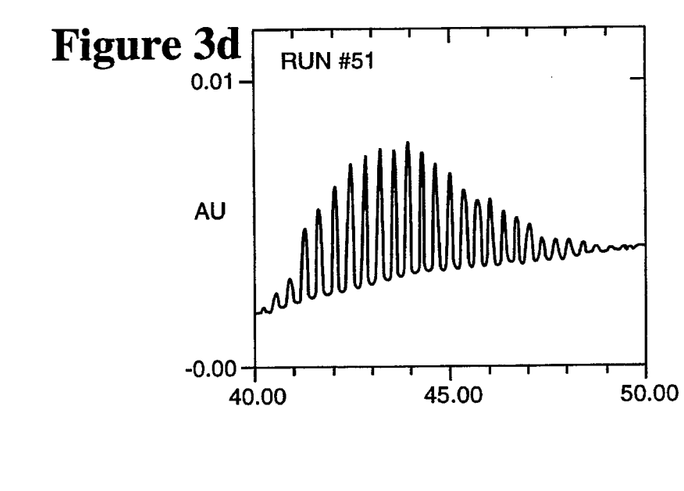
Figure 3E:
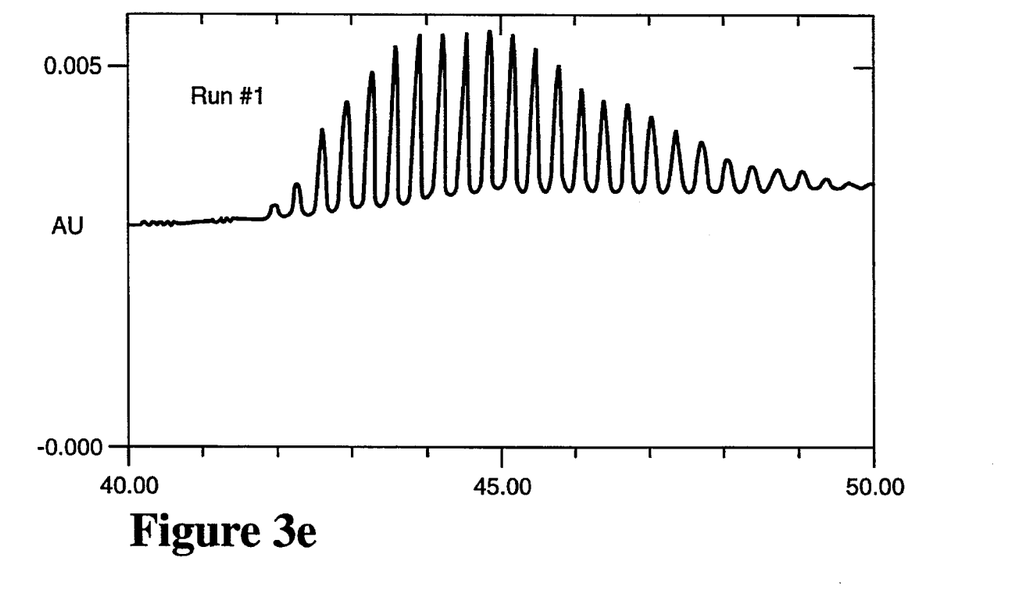
Figure 3F:
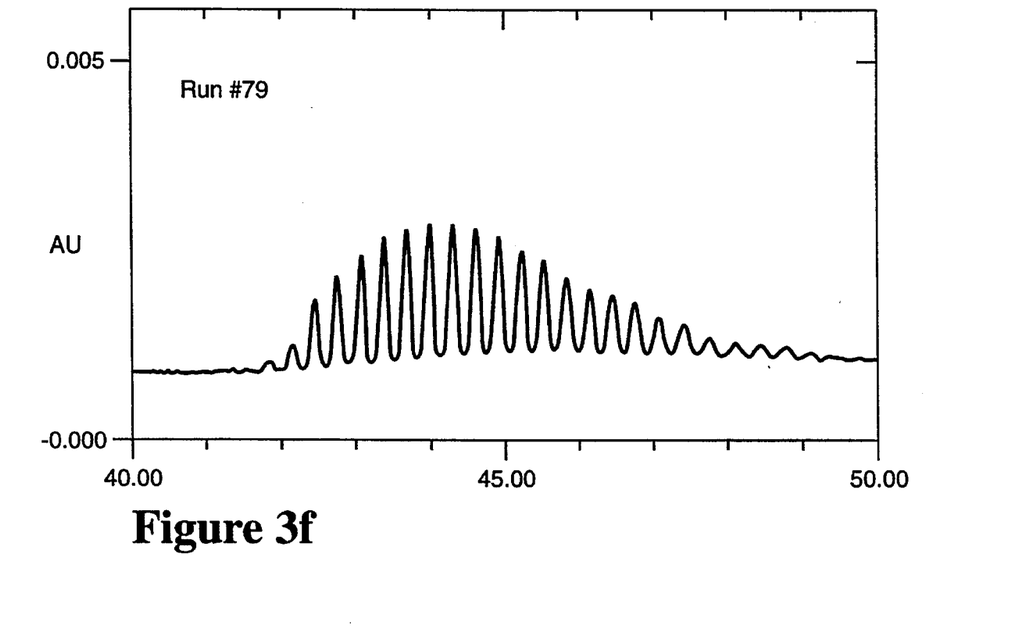
Figure 4A:
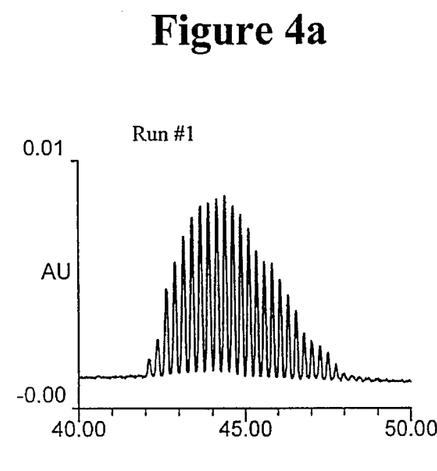
Figure 4B:
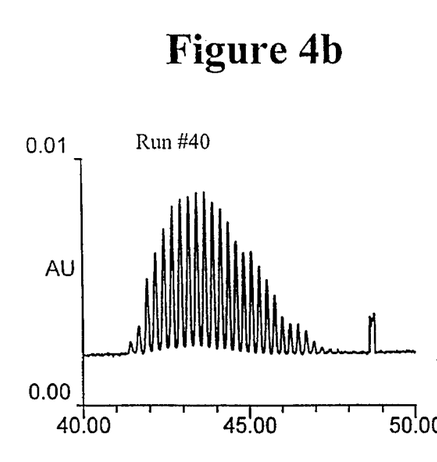
Figure 4C:
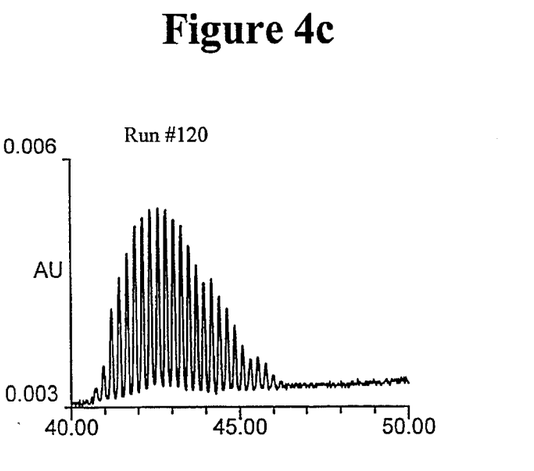
Figure 4D:
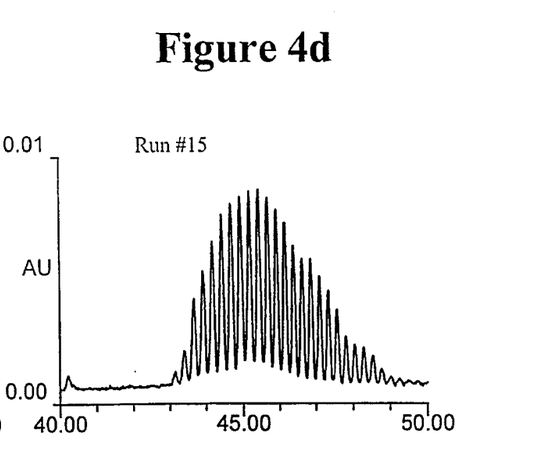

FIGS. 3A–F shows a gel-filled capillary used in capillary electrophoresis operated under one implementation of the polarity reversal protocol described in this invention. For this experiment, a 55 cm length of 75 μm id fused silica capillary containing a 5% T 5% C acrylamide gel with 1X TBE and 7M urea buffer was used. Oligomeric $pdA_{40-60}$ oligonucleotides (0.01 units/mL in 0.5X TBE) were injected at the anode end of the capillary for 12 successive 1-hour runs. The applied running voltage was 13 kV at a current of 8–10 μA and a power dissipation of 175 mW. Following each set of 12 1-hour separations, the polarity of the electrical field applied across the gel was reversed for one 12-hour (continuous) period of time. As evidenced by the demonstration separations selected from the data collected in this series of experiments, resolution of the $pdA_{40-60}$ oligonucleotides was maintained at essentially its original level (run #1) for an extended period of time. By way of example, run #1 and run #79 from this series of experiments are shown in FIGS. 3A and 3F, respectively; the two separations, which were performed on the same capillary approximately 6½ days apart, exhibit essentially identical migration times for the individual $pdA_{40-60}$ oligomer peaks in the samples. Furthermore, baseline resolution of the various components in the $pdA_{40-60}$ sample is maintained at run #79.

EXAMPLE 4

This example illustrates a gel-filled capillary operated under one hour normal polarity followed by one hour reversed polarity.

A 60 cm length of 100 μIc id fused silica capillary filled with a 6% T 5% C gel containing 1X TBE and 7M urea as buffer was operated at 15 kV applied potential and 15 μA current. An oligomeric $pdA_{40-60}$ nucleotide sample (0.01 units/mL) was electroinjected into the cathode end of the capillary and a 1-hour separation was carried out. At the conclusion of the separation, the polarity of the electrical field applied across the gel-filled capillary was reversed for one hour at 15 kV applied potential. This protocol of one hour normal polarity for separation followed by one hour reversed polarity was repeated for 150 cycles. FIGS. 4A–D shows representative separations selected from the data collected in this series of experiments and shows the resolution of the oligonucleotides was maintained at essentially the original level (run #1) for the 150 separations.

EXAMPLE 5

This example illustrates a gel-filled capillary operated continuously under normal polarity for extended period of time followed by regeneration of resolution in capillary under reversed polarity.

Figure 5A:
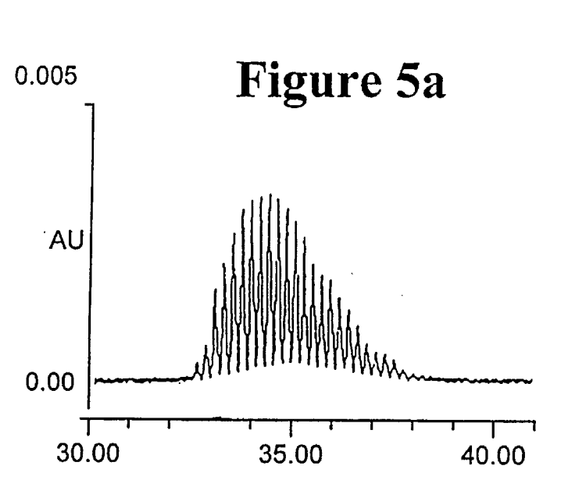
Figure 5B:
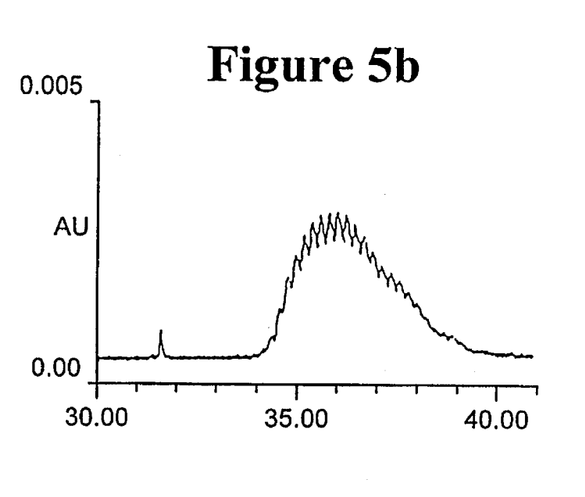
Figure 5C:
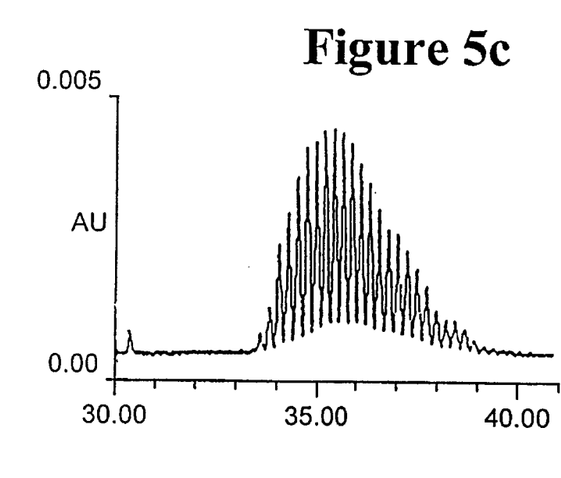
Figure 5D:
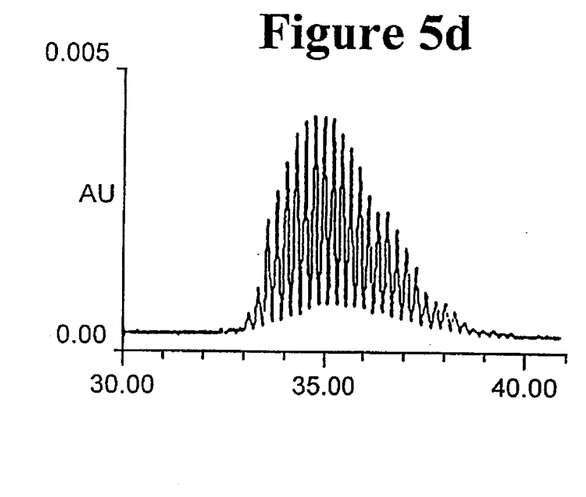

FIGS. 5A–D illustrates the benefits of polarity reversal in restoring a capillary that has been run for an extended period of time and has lost ability to resolve sample components. The capillary and most operating conditions used here are essentially identical to those in Example 1. The resolving capability of the capillary was first demonstrated by a number of separations of the $pdA_{40-60}$ oligonucleotide mixture; run #8 is included in FIG. 5A as an example of the initial resolving capability of the gel. After 33 one-hour runs on the capillary operated in continuous normal polarity mode, loss of resolution is evident as shown in FIG. 5B. At this point, the capillary was subjected to a polarity reversal protocol described in this invention; a reverse polarity of 13 kV was applied across the capillary gel for a continuous 995 minute period. Polarity was then restored to its normal configuration and repetitive injections of the $pdA_{40-60}$ oligonucleotide mixture were made; exemplary separations of the mixture are shown in FIG. 5C and 5D, which illustrates the restoration of the resolving capability of the capillary gel to near the initial level in FIG. 5A.

EXAMPLE 6

This example illustrates a gel-filled capillary operated under the protocol of changing the orientation of the gel.

Figure 6A:
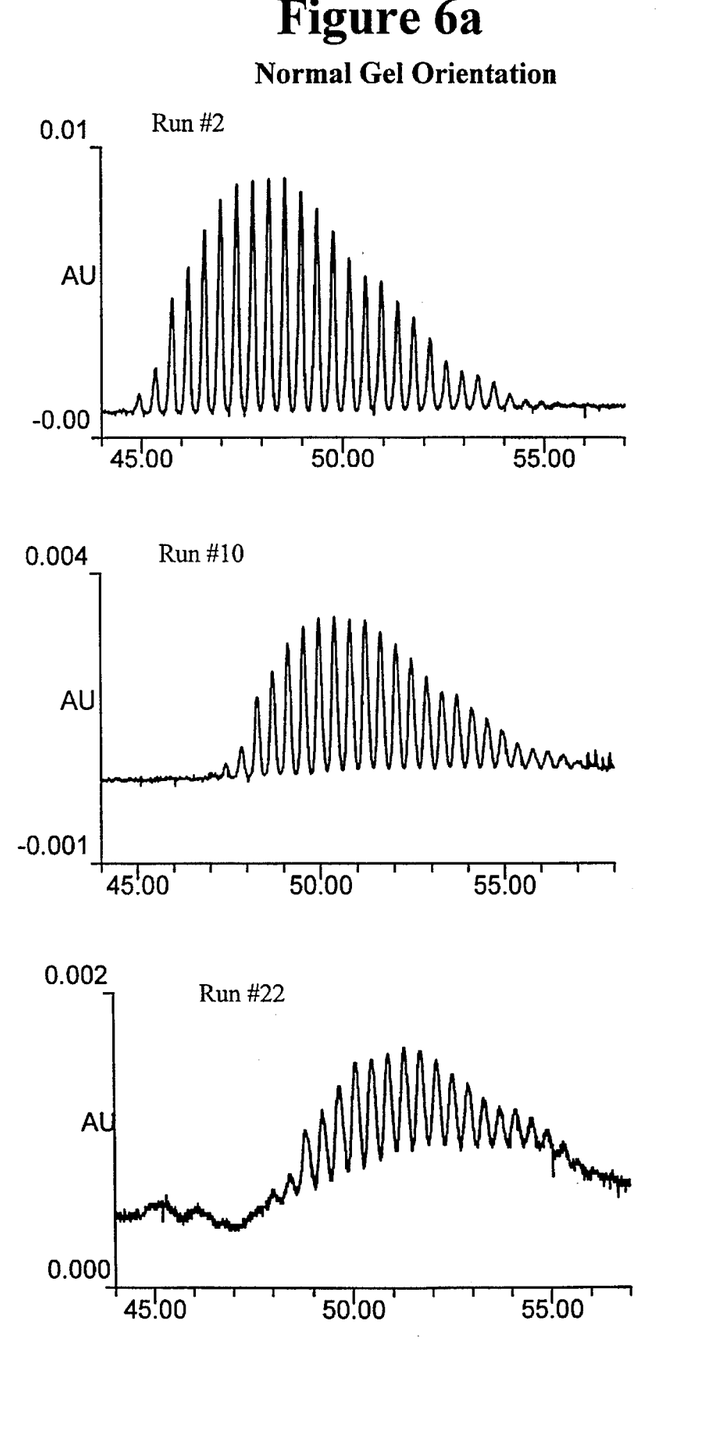
Figure 6B:
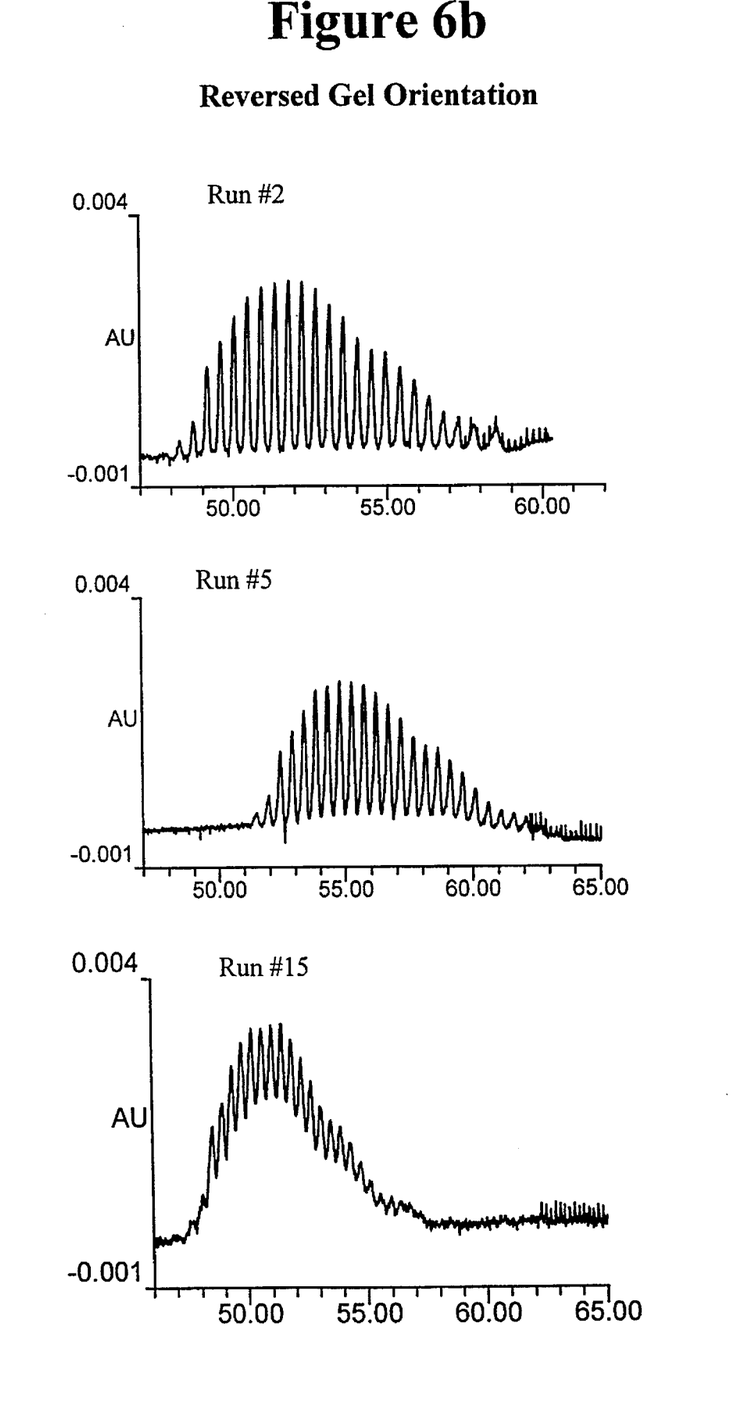
Figure 6C:
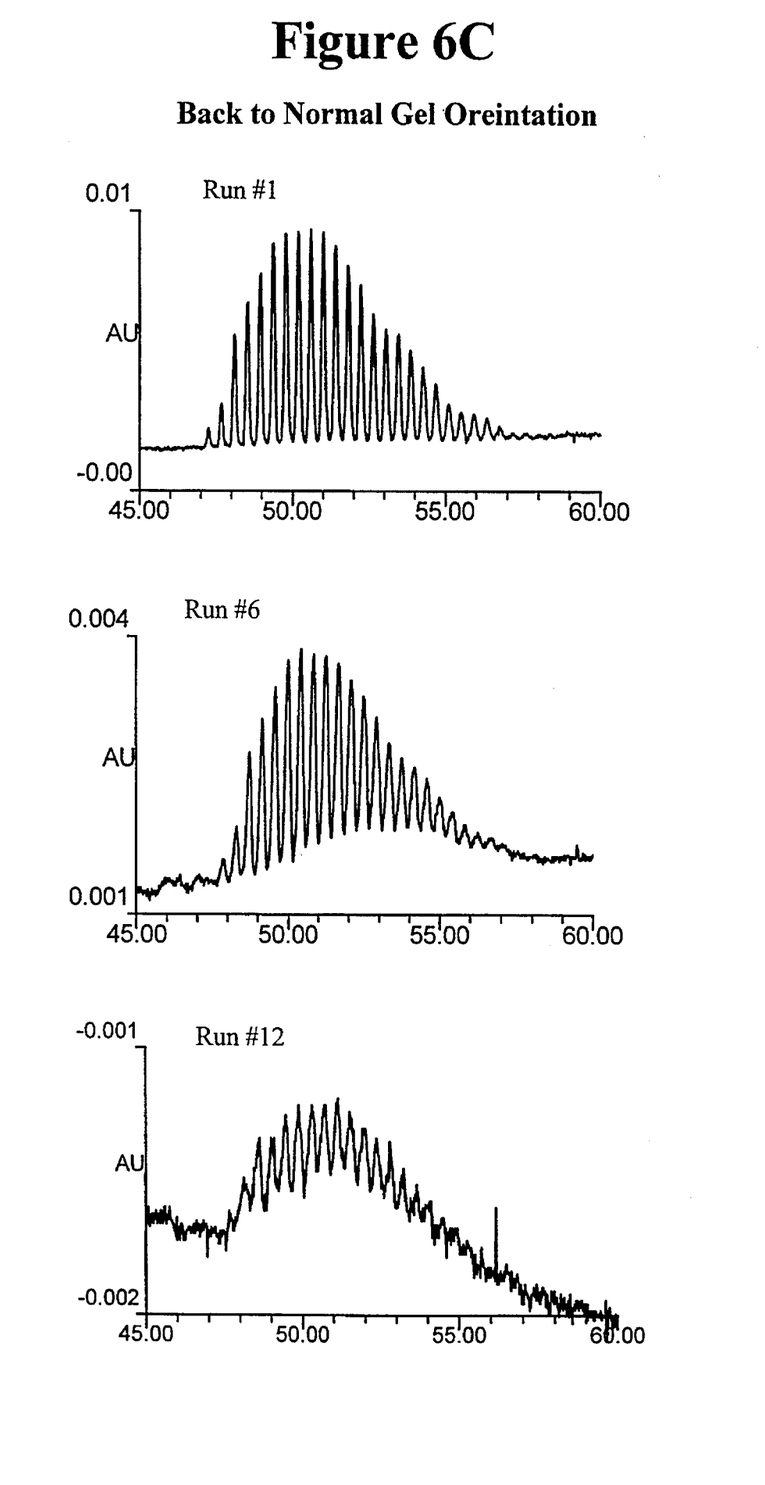

In this example, a 65-cm length of 100 μm id fused silica capillary filled with a 6% T 5% C gel containing 1X TBE and 7M urea as buffer was used. The applied running voltage was 15 kV. This gel-filled capillary had two detection windows located 5 cm from each end of the capillary. FIG. 6A shows the representative separation of $pdA_{40-60}$ oligonucleotides in the gel; the decrease in resolution of the component bands in the sample was significant after 22 sample runs. At that point, the orientation of the gel-filled capillary with respect to the applied electrical field was reversed such that the original cathode end of the gel-filled capillary was positioned in the anode buffer reservoir of the electrophoresis system and the original anode end of the gel-filled capillary was positioned in the cathode buffer reservoir. Oligonucleotide samples were then injected into the new cathode end of the gel-filled capillary and representative separations of the polyoligonucleotides in the reoriented capillary are shown in FIG. 6B. The resolution of the component bands was recovered following the change in orientation of the capillary. The gel-filled capillary again lost resolution after about 15 sample runs and the capillary was returned to its original orientation with respect to the electrical field. Injection of the $pdA_{40-60}$ oligonucleotide sample was made into the original cathode end of the capillary and FIG. 6C demonstrates the recovery of the resolution of the oligonucleotide bands in the gel-filled capillary in this (original) orientation with respect to the electric field.

EXAMPLE 7

This example illustrates improved reproducibility of analyte migration times for capillaries operated with reversed polarity protocol.

Figure 7A:
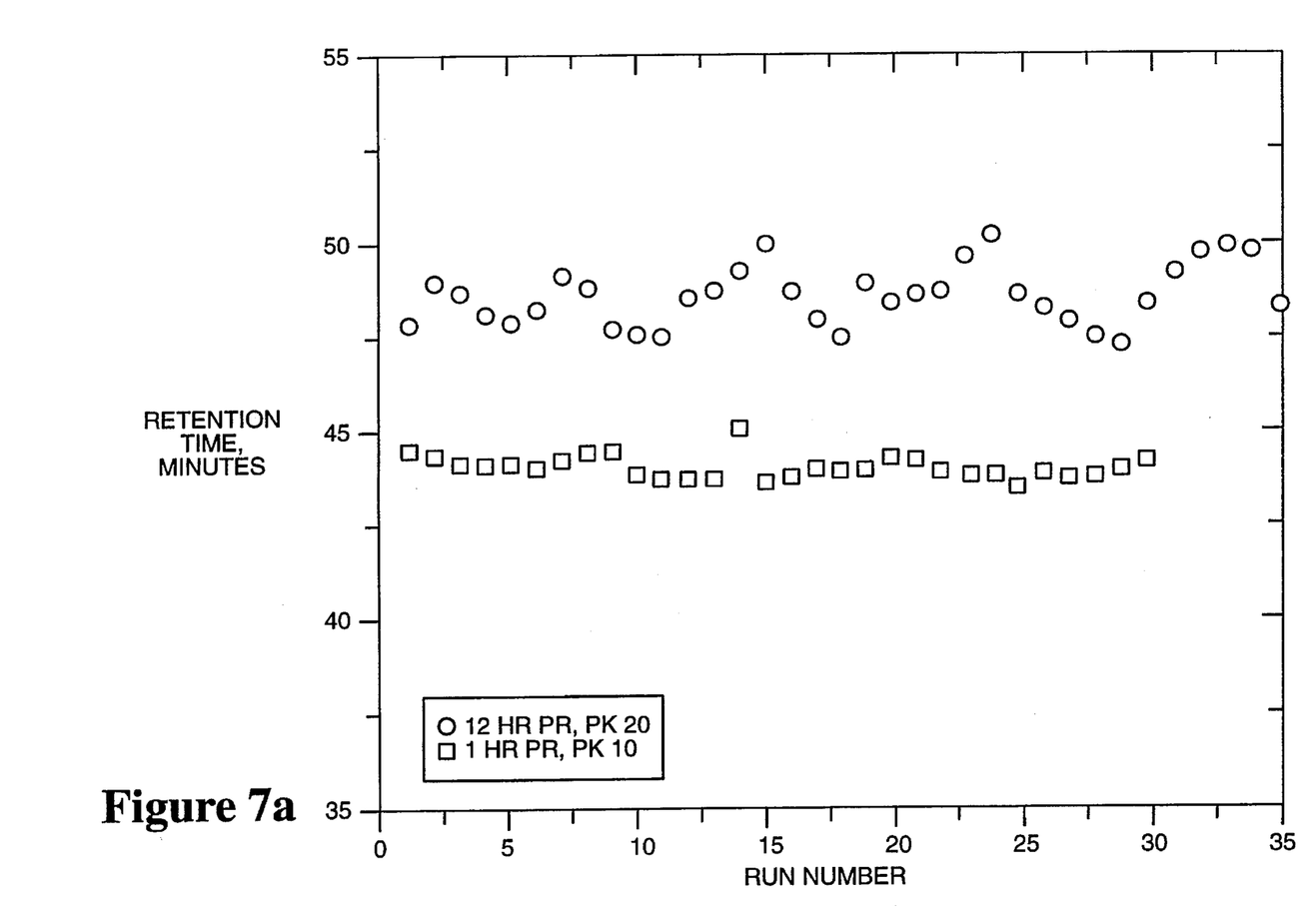
Figure 7B:
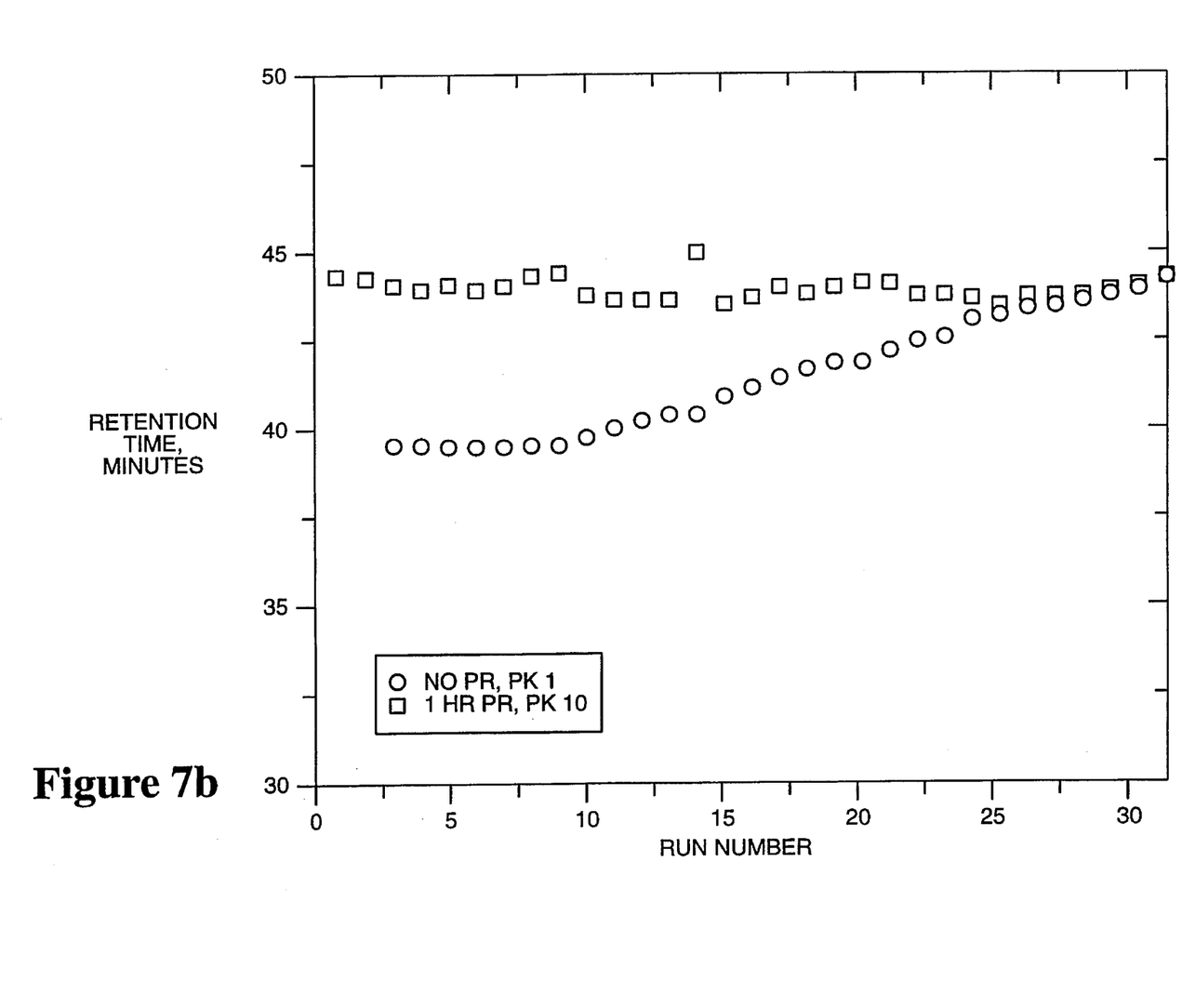

FIG. 7A and FIG. 7B illustrate the stability of elution times of representative peaks from the $pdA_{40-60}$ oligonucleotide samples separated on gel-filled capillaries operated with normal polarity under the conditions given in Example 1, and operated with the protocols of polarity reversal given in Examples 2 and 3. FIG. 7A shows that the migration time of a $pdA_{40-60}$ oligonucleotide increases with time as the number of sample runs made on a gel-filled capillary increases if no polarity reversal is implemented, whereas the migration time of an oligonucleotide is much more stable over the same period of time when a protocol of 1-hour polarity reversal is used. The data in FIG. 7B indicate that the migration time of an oligonucleotide is more stable when a capillary is operated with a protocol of 1-hour polarity reversal relative to a capillary operated with a protocol of 12-hour polarity reversal.

What is claimed is:

1. A method for gel electrophoresis in which a same gel is reused for the sequential separations of multiple samples and the useful life of the gel is extended by periodic reversal of the polarity of the applied electric field along the gel, said method comprising (a) depositing a first sample at a first end of an electrophoretic gel having a gel flow path which has a first and second end, (b) electrophoretically separating macromolecules in said first sample along said gel flow path by applying an electric field along said gel flow path, (c) detecting said separated first sample macromolecules on line during step (a), (d) eluting said separated first sample macromolecules from said gel flow path, (e) applying an electric field along said gel flow path of opposite polarity to that applied in step (a), (f) then, electrophoretically separating macromolecules in a second sample through said electrophoretic gel flow path by depositing said second sample at said first or second end while applying an electric field along said gel flow path of said gel, and (g) detecting the macromolecules in said second sample on line during step (e).

2. The method of claim 1 in which said electrophoretic gel is disposed in a conduit and said gel flow path is through said conduit.

3. The method of claim 2 in which said conduit is a capillary.

4. The method of claim 1 further comprising, after step (c) and prior to step (d), electrophoretically separating macromolecules in a third sample by depositing said third sample at said first or second end while applying an electric field along said gel flow path.

5. The method of claim 1 in which during step (b) the macromolecules of a third sample are electrophoretically separated by depositing said third sample at said second end during application of said electric field.

6. The method of claims 1 in which in step (b) said electric field of opposite polarity is applied by reversing the orientation of said gel flow path without modifying the polarity of the electric field.

7. The method of claim 1 in which in step (b) the orientation of the electrophoretic gel is reversed from step (a) without modifying the polarity of the electric field.

8. A method for gel electrophoresis in which a gel is reused for the sequential separations of multiple samples and the useful life of the gel is extended by periodic reversal of the polarity of the applied electric field along the gel, said method comprising (a) depositing a first sample at a first end of an electrophoretic gel having a gel flow path which has a first and second end (b) electrophoretically separating macromolecules in said first sample along said gel flow path by applying an electric field along said gel flow path, (c) detecting said separated first sample macromolecules on line during step (a), (d) eluting said separated first sample macromolecules from said gel flow path, and (e) then, electrophoretically separating macromolecules in a second sample through said electrophoretic gel flow path by depositing said second sample at said second end and applying an electric field along said gel flow path of said gel of opposite polarity to that applied in step (a).

9. The method of claim 7 in which said electrophoretic gel is disposed in a conduit and said gel flow path is through said conduit.

10. The method of claim 9 in which said conduit is a capillary.

* * * * *